(12) United States Patent
Blackmore (10) Patent No.: US 10,046,412 B2
(45) Date of Patent: Aug. 14, 2018

(54) METHOD OF MANUFACTURING A COMPONENT

(71) Applicant: ROLLS-ROYCE PLC, London (GB)

(72) Inventor: Michael Lewis Blackmore, Sheffield (GB)

(73) Assignee: ROLLS-ROYCE PLC, London (GB)

( * ) Notice: Subject to any disclaimer, the term of this patent is extended or adjusted under 35 U.S.C. 154(b) by 857 days.

(21) Appl. No.: 14/337,566

(22) Filed: Jul. 22, 2014

(65) Prior Publication Data
US 2015/0034606 A1    Feb. 5, 2015

(30) Foreign Application Priority Data

Aug. 2, 2013   (GB) .................................... 1313839.1

(51) Int. Cl.
*B23K 15/00* (2006.01)
*B23K 15/02* (2006.01)
(Continued)

(52) U.S. Cl.
CPC ............ *B23K 15/02* (2013.01); *B22F 3/1055* (2013.01); *B23K 15/0026* (2013.01); *B23K 15/0086* (2013.01); *G01N 23/203* (2013.01); *B22F 2003/1057* (2013.01); *G01N 2223/102* (2013.01); *G01N 2223/62* (2013.01); *Y02P 10/295* (2015.11)

(58) Field of Classification Search
CPC ........................... B23K 15/00; B23K 15/0046; B23K 15/0086; B23K 26/342
USPC ... 219/121.6, 121.7, 121.35, 121.65, 121.66, 219/121.83, 121.85
See application file for complete search history.

(56) References Cited

U.S. PATENT DOCUMENTS

| 2004/0019403 A1* | 1/2004 | Liu ......................... B41J 2/161 700/166 |
| 2009/0152771 A1 | 6/2009 | Philippi et al. |

(Continued)

FOREIGN PATENT DOCUMENTS

| WO | WO 2010/069037 A1 | 6/2010 |
| WO | 2015/091813 A1 | 6/2015 |

OTHER PUBLICATIONS

Apr. 20, 2017 Office Action issued in European Patent Application No. 14178255.7.
(Continued)

*Primary Examiner* — Michael Laflame, Jr.
(74) *Attorney, Agent, or Firm* — Oliff PLC (57) ABSTRACT

A method of manufacturing a component includes providing a powder layer; scanning the powder layer using an electron beam; detecting back scattered electrons produced by the interaction of the electron beam with the powder layer; identifying, from the detected back scattered electrons, any defects in the powder layer; selectively melting at least a part of the powder layer so as to generate a solid layer; and repeating these steps at least once so as to build up a shape corresponding to the component. The method may also includes steps of making a decision about whether to remove any identified defects in the powder layer, and adjusting one or more parameters of the step of providing a powder and/or adjusting one or more parameters of the selective melting step so as to avoid future recurring defects at that position based on stored data relating to the scanned powder layer.

20 Claims, 6 Drawing Sheets

(51) Int. Cl.
*B22F 3/105* (2006.01)
*G01N 23/203* (2006.01)

(56) References Cited

U.S. PATENT DOCUMENTS

2010/0068512 A1* 3/2010 Imaoka ................. B82Y 30/00
428/336
2013/0055568 A1 3/2013 Dusel et al.

OTHER PUBLICATIONS

Search Report issued in British Application No. 1313839.1 dated Mar. 21, 2014.
Dec. 8, 2014 Search Report issued in European Application No. EP 14 17 8255.

* cited by examiner

METHOD OF MANUFACTURING A COMPONENT

CROSS-REFERENCE TO RELATED APPLICATIONS

This application is based upon and claims the benefit of priority from British Patent Application Number 1313839.1 filed 2 Aug. 2013, the entire contents of which are incorporated by reference.

BACKGROUND OF THE INVENTION

1. Field of the Disclosure

The present invention relates to a method of manufacturing a component. In particular, the present invention relates to manufacturing a component using additive layer manufacture.

2. Description of the Related Art

Additive layer manufacturing (ALM) methods (for example using electron beam melting (EBM)) may be used to manufacture metallic components by sequential selective melting of thin metal powder layers. According to such a method, a layer of powder (such as metal powder) is deposited onto a surface (or plate), and an energy source (such as an electron beam) is used to selectively melt the powder layer. The melted material then solidifies so as to form a solid layer of the desired shape. A further layer of powder is then deposited, and the energy source is used to selectively melt the further powder layer, which then solidifies to form another solid layer of the desired shape onto the previous solid layer. The process is repeated until the final 3D geometry has been built up by selective melting and solidification of multiple layers.

The process can operate directly from a 3D CAD model of the geometry to be manufactured, and may not require any specific tooling to be produced for a particular geometry or component. Accordingly, ALM can be used to generate parts having complex 3D free form geometry, with short lead times.

Typically, a 3D CAD model of the geometry to be produced is virtually sliced into a series of thin, pseudo 2D, slices equal to the layer thickness generated when the electron beam melts a single powder layer. The thin slices of the geometry are then used to generate an electron beam melting path for each layer. This process may be used as part of or along with the present invention.

An energy beam may use any desired path for melting each layer. For example, the contour (or outline) of the layer may first be melted by the beam, and then the bulk of the layer may be melted, for example by hatching, i.e. rastering the beam back and forth along parallel vectors. Once a layer has been completed, the partially manufactured component may be stepped downwards, away from the electron beam, to allow the next powder layer to be deposited and melted.

OBJECTS AND SUMMARY

Manufacturing components using ALM has many advantages, including the possibility to manufacture complex 3D shapes with little or no bespoke tooling, but the final components can have defects. Such defects may result in undesirable properties, and may limit the use of the finished components to certain applications and/or necessitate further processing steps (such as hot isostatic pressing, or HIP) to remove the defects in order for the components to have the required properties for a given application.

It is therefore desirable to produce components using ALM that have fewer and/or smaller defects.

According to an aspect, there is provided a method of identifying defects during manufacture of a component using additive layer manufacture. The method comprises providing a powder layer to be melted in order to produce a layer of the component. The method comprises scanning the powder layer using an electron beam. The method comprises detecting back scattered electrons produced by the interaction of the electron beam with the powder layer. The method comprises identifying, from the detected back scattered electrons, any defects in the powder layer to be melted.

Accordingly, the present invention allows defects in the powder layer to be detected prior to melting of the powder layer. The method may be said to comprise inspecting the powder layer. It has been recognised that any defects in the powder layer may result in defects in the solidified layer after melting, and thus in the finished component. Therefore, detecting any defects in the powder layer prior to melting may be advantageous, for example in controlling and/or understanding the properties of the finished component.

The defects in the powder layer may be due to an inconsistent powder layer. The present invention may enable detection of an inconsistent powder layer. Such inconsistency may be in, for example, the thickness and/or particle size of the powder layer. The present invention may allow the position and/or size and/or type of defect to be identified. For example, such a type of defect that may be detected may include thick or thin powder layer defects (for example where the powder layer is thicker or thinner than desired) and/or so-called swelling defects, in which the previously melted and solidified layer extends through the powder layer being scanned.

Additionally or alternatively, a defect in the powder layer may be due to the presence of an unwanted foreign body or particle in the layer. Such a foreign body may be from a part of the ALM machine, which may fall in to the powder layer in error. For example, such a foreign body may be a part of a tooth from a rake used to spread the powder layer, or a flake of condensate from a heat shield of the ALM machine. Such foreign bodies would typically have different density to the particles, and may be readily detected by the electron beam.

Detecting defects in the powder layer may help to reduce the number/percentage of defective for example scrap) components that are generated using ALM/EBM techniques, resulting in cost and/or efficiency savings. If a defect is detected during the manufacturing process rather than after the manufacturing process, a decision on the fate of the component (for example based on whether the powder layer defect can be and/or needs to be addressed) can be made before the remainder of the component is manufactured. This may further add to cost and/or efficiency savings.

The electron beam used to scan the powder layer may be considered to be a scanning electron microscope and may act as a scanning electron microscope.

The power of the electron beam used to scan the powder layer may be insufficient to cause melting of the powder layer.

According to an aspect there is provided a method of manufacturing a component using additive layer manufacture. The method comprises performing the steps of: providing a powder layer; scanning the powder layer; detecting back scattered electrons; and identifying defects in the powder layer as described above and elsewhere herein. The method comprises selectively melting at least a part of the powder layer so as to generate a solid layer of the component. The steps of: providing a powder layer; scanning the powder layer; detecting back scattered electrons; identifying defects in the powder layer; and selectively melting at least a part of the powder layer may be repeated at least once so as to build up a shape corresponding to the component.

In the context of manufacturing a component using ALM (which, as described elsewhere herein, may be EBM), the step of identifying defects in the powder layer or inspecting the powder layer) is performed before selective melting of that powder layer.

The component may be said to be manufactured in a "layerwise" manner, that is to say by forming one solid layer on top of another layer. The component may be a metallic component. The built-up shape corresponding to the component may actually be the component itself, or may be a shape that requires one or more further manufacturing and/or finishing steps (such as, by way of example only, machining or HIP) in order to produce the final component. The part-built component may be moved (or stepped) away from the electron beam source before the next layer of powder material is provided.

According to an aspect, there is provided an additive layer manufacture machine (which may be an EBM machine) for manufacture a component. The machine comprises a powder delivery device for delivering successive layers of powder to be melted. The apparatus comprises an electron beam source for generating a scanning electron beam to scan the powder layer. The apparatus comprises a backscatter detector for receiving backscattered electrons resulting from the interaction of the scanning electron beam with the powder layer. This allows any defects in the powder layer to be detected. The apparatus comprises an energy source for generating heat for selectively melting at least a part of the powder layer so as to produce a solid layer of the component. The apparatus may also comprise a base plate on which the component is manufactured. The apparatus may also comprise a powder delivery device for delivering successive layers of powder (for example onto the baseplate and/or onto previously melted and solidified layers of the component).

In all aspects, the powder layer may be an electrically conductive powder layer. The powder layer may comprise any electrically conductive particles, for example any particles whose surface at least is electrically conductive. The powder layer may be a metal powder layer. The solid layer may be a solid metallic layer. A metal powder layer may comprise any desired metallic powder grains or particles. For example, the metal powder may comprise solid metal particles and/or metal-coated particles.

An energy beam may be used to selectively melt at least a part of the powder layer. Such an energy may be, by way of example only, a laser beam or an electron beam.

Thus, an electron beam may be used to selectively melt at least a part of the powder layer. In such an arrangement, the electron beam used to scan the powder layer may be referred to as a first electron beam, or a scanning electron beam, and the electron beam used to selectively melt at least a part of the powder layer may be referred to as a second electron beam or a melting electron beam. The power of the first (scanning) electron beam may be lower than the power of the second (melting) electron beam. Additionally or alternatively, the intensity (for example the peak intensity) of the first (scanning) electron beam may be lower than the intensity (for example the peak intensity) of the second (melting) electron beam. The power (and/or intensity) of the second (melting) electron beam may be sufficient to melt the powder layer as desired, whereas the power (and/or intensity) of the first (scanning) electron beam may be insufficient to melt the powder layer.

Where an electron beam is used both to scan the powder layer and to selectively melt the powder layer, the electron beam source for generating the first (scanning) electron beam may be the same as the electron beam source for generating the second (melting) electron beam. For example, at least one parameter may be changed for generating the second beam as opposed to the first beam, such as the power used by the source to generate the beams. This may result in a particularly compact and/or low cost additive layer manufacturing machine.

Alternatively, the electron beam source for generating the first electron beam may be different to the electron beam source for generating the second electron beam. Nevertheless, the two electron beam sources may be a part of the same additive layer manufacturing machine.

Where a second (melting) electron beam is used to selectively melt at least a part of the powder layer, more than one area of the powder layer may be selectively melted substantially simultaneously. In this way, the selective melting step may comprise generating multiple melt pools in the powder layer substantially simultaneously. Purely by way of example, up to 50 or 100 melt pools may be generated simultaneously. This may be achieved in any suitable manner. For example, the melting electron beam may be rapidly moved around the powder layer to generate multiple weld pools substantially simultaneously. Additionally or alternatively, the melting electron beam may in fact comprise multiple beams that are focussed on the powder layer substantially simultaneously in order to generate multiple weld pools at a given time. Such multiple beams, where used, may be generated by splitting a single generated beam or by generating multiple beams, for example. Where present, such multiple beams fall within the term "second (or melting) electron beam" as used herein.

Identified defects in the powder layer may be removed prior to selectively melting at least a part of the powder layer. Any one or more defects may be removed. Selected defects or all defects may be removed, as desired. The defects may be removed from the powder layer in any suitable manner, for example by re-raking and/or re-laying the powder layer (which may or may not involve firstly removing the layer of powder in which the defects have been detected) and/or by removing the layer of powder and selectively re-melting a part of the previously melted layer.

Removal of defects at this stage may be advantageous in producing a finished component with improved properties, for example with reduced porosity and/or better strength. Additionally or alternatively, the finished component may have a greater chance of conforming with the design specification.

If a defect is identified in the powder layer, a decision about whether or not to remove any identified defects in the powder layer may be taken. Such a decision may be taken before selectively melting at least a part of the powder layer. The decision may be based on one or more predetermined criteria. Such a decision may result in a defect being removed for example by any one of the techniques described above and elsewhere herein. The decision may result in no action being taken, for example if a defect is deemed to be within an acceptable tolerance such that it would not result in an unacceptable defect in the finished component.

The decision may be based at least in part on the size of the defect. For example, the decision may be based at least in part on the height of a swelling defect and/or the height/ depth of a thick/thin layer defect. In this regard, the scanning (first) electron beam may be able to determine a 3-D shape of the powder layer, and thus a 3-D shape of any defects.

Additionally or alternatively, the decision may be based on the location and/or the shape of the defect.

The decision may taken by a machine, for example without human intervention. Thus, the decision may be an automated decision, which may be based on one or more criteria, such as those described above and elsewhere herein.

Alternatively, the decision may be taken by an operator of the machine. Alternatively still, the decision may be taken by a combination of machine and operator. For example, the machine may automatically identify potential defects that may require corrective action, and an operator may take the final decision on whether any action is required.

Data relating to the scanned powder layer may be stored/recorded (for example electronically). For example, the location and/or shape/size of any identified defects may be recorded. Such location information may include, for example, the powder layer in which the defect was identified and the position within that layer. The data relating to the scanned powder layer may be recorded regardless of whether or not the defect is subsequently removed.

The stored data may be used to determine whether any defects have been identified at the same position within the respective layers of two or more different powder layers, such defects being recurring defects. If any such recurring defects have been identified, one or more parameters of the step of providing a powder (the powder delivery step) and/or the selective melting step may be adjusted so as to avoid future recurring defects at that position. Such parameters may include, for example, the speed and/or path of the powder delivery, the power and/or intensity of the selective melting (for example the power or local power of an energy beam used to perform the selective melting) and/or the scanning (or rastering) speed and/or the path (including the turning positions and/or rates) of an energy beam used to perform the selective melting An image of the scanned powder layer may be generated, including any identified defects in the powder layer. The image may be stored for future reference. The image may be used to decide on the fate of the component, for example whether to remove any defects, and if so how to remove the defects.

After selective melting of the powder layer, the method may comprise identifying any defects in the solid layer by scanning the solid layer using a solid layer scanning electron beam and detecting back scattered electrons produced by the interaction of the solid layer scanning electron beam with the solid layer.

Where an electron beam is used to perform the selective melting, the power (and/or intensity) of the solid layer scanning electron beam may be lower than the power (and/or intensity) of the electron beam used to perform the selective melting. The power of the solid layer scanning electron beam may be insufficient to cause additional, unwanted, melting. The solid layer scanning electron beam may the same as the electron beam used to scan the powder layer before selective melting.

An additive layer manufacturing machine as described above and elsewhere herein according to the invention for manufacturing a component may comprise an electron beam source for generating such a solid layer scanning electron beam. Such an apparatus would comprise a backscatter detector for receiving backscattered electrons from the surface of the solid layer resulting from the scan by the solid layer scanning electron beam to identify any defects in the solid layer. The same electron beam source may be used to generate any one or more of the electron beam used to scan the powder layer, the melting electron beam and the solid layer scanning electron beam, where present. The same backscatter detector may be used to detect backscatter electrons from interactions resulting from the electron beam used to scan the powder layer and the solid layer scanning electron beam. Alternatively, dedicated backscatter detectors may be used with each electron beam.

The optional use of a solid layer scanning electron beam allows any defects in the solid layer to be detected in-situ. For example, any defects associated with a particular solid layer can be detected before the next layer of powder is supplied and melted. As such, even if the powder layer is determined to be defect free before selective melting, any defects that occur during the melting process may be detected. Such defects may be melt-related defects in line with the stochastic natural of distributing and melting tens of millions of powder grains with small variations in process parameters and powder particles. Additionally or alternatively, defects may be caused by unsuitable selection of process parameters, such as inappropriate rastering speed.

Detecting any defects in the solid layer before the next layer of powder is supplied and melted may help to further reduce the number/percentage of defective (for example scrap) components that are generated using ALM/EBM techniques, resulting in cost and/or efficiency savings. If a defect in the solid layer is detected during the manufacturing process rather than after the manufacturing process, a decision on the fate of the component (for example scrap, fixable, within tolerance) can be made before the remainder of the component is manufactured. This may further add to cost and/or efficiency savings.

Where a solid layer scanning electron beam is used, the method may comprise removing any identified defects in the solid layer before providing the next powder layer. Such a step of removing any identified defects in the solid layer may comprise using the melting electron beam to re-melt at least a part of the solid layer (for example re-melting the region of and/or around the defect, or re-melting the entire layer). This may include melting any powder that was left unmelted in error. Removing any identified defects may result in higher quality components and/or a reduced percentage of scrapped components and/or a more efficient process.

After any defects have been removed, the method may comprise re-scanning at least a part of the solid layer using the solid layer scanning electron beam to confirm that the identified defects have been removed. For example, the entire solid layer may be re-scanned, or just the region(s) around any defect(s) may be re-scanned.

As with data relating to the scanned powder layer, data relating to the scanned solid layer may be stored/recorded (for example electronically). For example, the location and/or shape/size in the component of any identified defects in the solid layer may be recorded. Such location information may include, for example, the layer in which the defect was identified and the position within that layer. The data relating to the layer scanned by the solid layer scanning electron beam may be recorded regardless of whether or not the defect is subsequently removed. This may avoid the need to perform additional inspection or testing after the component has been manufactured.

The stored data may be used to determine whether any defects have been identified at the same position within the respective layers of two or more different solid layers, such defects being recurring defects. If any such recurring defects have been identified, one or more parameters of the selective melting step may be adjusted so as to avoid future recurring defects at that position. For example, where a melting electron beam is used in the selective melting step, such parameters may include, for example, the power and/or intensity of the melting electron beam (for example the local power) and/or the scanning (or rastering) speed of the melting electron beam, and/or the path (including the turning positions and/or rates) of the melting electron beam.

The method may comprise generating an image of the solid layer, including any identified defects in the solid layer. The image may be stored for future reference. The image may be used to decide on the fate of the component, for example whether to remove any defects shown in the image, whether to scrap the component, or whether to proceed without taking any action (for example because any defects are within an acceptable tolerance).

If a defect is identified in the solid layer, the method may further comprise making a decision about whether or not to remove any identified defects in the solid layer before providing the next powder layer. The decision may be based on one or more predetermined criteria. Such a decision may result in a defect being removed by re-melting, as described above and elsewhere herein. The decision may result in no action being taken, for example if a defect in the solid layer is deemed to be within an acceptable tolerance.

The decision may be based at least in part on the size of the defect in the solid layer. For example, the decision may be based at least in part on the surface area and/or the depth of the defect in the solid layer. In this regard, the solid layer scanning electron beam may be able to determine a 3-D shape of the solid layer, and thus a 3-D shape of any defects.

Additionally or alternatively, the decision may be based on the location and/or the shape of the defect.

The decision may taken by a machine, for example without human intervention. Thus, the decision may be an automated decision, which may be based on one or more criteria, such as those described above and elsewhere herein.

Alternatively, the decision may be taken by an operator of the machine. Alternatively still, the decision may be taken by a combination of machine and operator. For example, the machine may automatically identify potential defects that may require corrective action, and an operator may take the final decision on whether any action is required.

Embodiments of the invention will now be described with reference to the accompanying drawings, in which:

DETAILED DESCRIPTION OF THE PREFERRED EMBODIMENTS

As explained elsewhere herein, additive layer manufacturing (ALM) methods may be used to manufacture components by sequential selective melting of thin powder layers. For example, an EBM machine may be used to manufacture a metallic component by sequential selective melting of thin metal powder layers.

Figure 1:
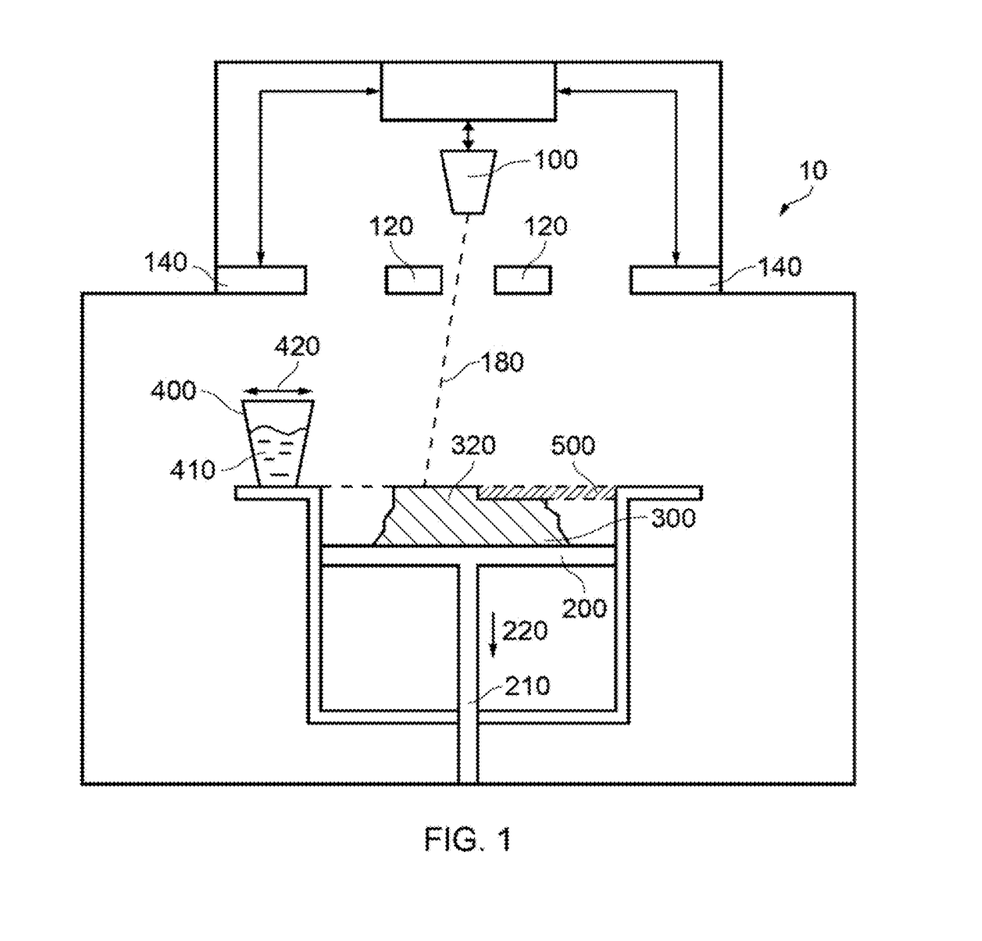
FIG. 1 shows an additive layer manufacture machine in accordance with the invention being used to selectively melt a powder layer.

An example of an additive layer manufacturing machine (or ALM machine) 10 for use in such a method is shown in FIG. 1. The ALM machine 10 comprises an electron beam source 100 for generating an electron beam 180 (which may be referred to as a melting electron beam, or second electron beam 180). In use, the electron beam 180 is focussed (and optionally split) using focusing elements 120, such as lenses and/or mirrors, towards a component 300 being manufactured. Specifically, the electron beam 180 is focussed onto a layer of powder (for example a layer of powder metal) 500 to be melted by the electron beam 180 which subsequently melts to form a solid layer (for example a solid metal layer) of the component 300. The electron beam 180 is an example of an energy beam used to selectively melt the powder layer 500. The interior of the ALM machine 10, or at least the part of the interior of the ALM machine 10 through which electron beams travel may be a vacuum, or at least a partial vacuum.

In operation, the melting electron beam 180 scans over the metal powder layer 500 in a desired pattern so as to selectively melt the metal powder layer 500 in the correct shape required to manufacture that particular layer, or slice, of the component 300. The melted metal then solidifies to form a layer 320 of the component 300 in the desired shape. Thus, at least a part of the metal powder layer 500 is brought into a temporary molten state by the energy provided by the melting electron beam 180 such that when the material solidifies it forms at least part (in the form of a layer) of the component 300 being manufactured.

In FIG. 1, a part of the powder layer 500 has been selectively melted and solidified so as to form a part of a solid layer 320 of the component 300. Thus, FIG. 1 shows the component 300 part way through selective melting of the powder layer 500 to form the latest solid layer 320.

The component 300 may sit on a base plate 200 that sits on a translatable support 210, as in the FIG. 1 example. The translatable support 210 may be moved using any suitable means in a direction 220 that is substantially perpendicular to the layers 320 of the component 300. After each layer 320 is completed, the translatable support 210 moves by a predetermined distance in the direction 220 that is substantially perpendicular to the layer 320. Thus, the base plate 200 and the component 300 also move in the direction 220, and may be said to be indexed downwards (for example away from the electron beam source 100).

After the translatable support 210 has been indexed downwards, another layer of metal powder 500 is supplied on top of the previous completed, solidified, layer 320. Purely by way of example, a hopper 400 containing metal powder 410 may be moved across the top of the previous solidified layer 320, depositing the next layer of powder material 310 as it moves, as shown in FIG. 1 by way of example. In FIG. 1, the direction arrow 420 indicates the direction of movement of the hopper 400 across the component 300. Of course, the hopper 400 may move relative to the component 300 in directions other than indicated by arrow 420 in FIG. 1, for example to ensure full (or the desired) coverage of metal powder 410 in a metal powder layer 310. Such a process may be known as powder bed deposition. However, any other method or system may be used to deposit the next layer of powder material 310 without impacting upon any other aspect or feature of the invention. For example, the hopper 400 containing the metal powder 410 may be fixed, and the powder 410 may be distributed into a layer 310 using a powder spreading device (not shown). Such a powder spreading device may comprise a rake that collects powder from a hopper and then distributes the powder over the support 210 or previously solidified layer 320 (which may be collectively referred to as the build area).

According to an aspect of the invention, after a powder layer 500 has been deposited, it is inspected before selective melting to form the next solidified layer 320. An example of such an inspection of the powder layer 500 is shown in FIG. 2.

Figure 2:
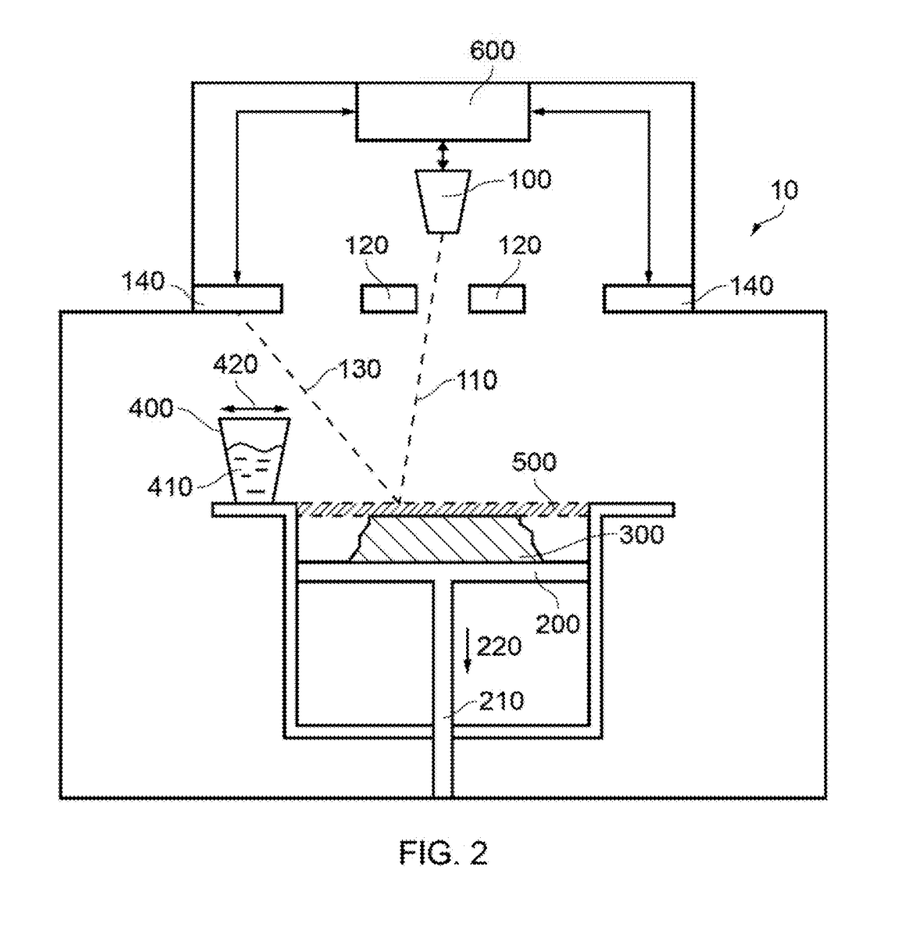
FIG. 2 shows an additive layer manufacture machine in accordance with the invention being used to detect defects in a powder layer.

In FIG. 2, an electron beam 110 (also referred to as a first electron beam or a scanning electron beam 110) is focused on the powder layer 500, prior to selective melting of the powder layer 500. The interaction between the scanning electron beam 110 and the powder layer 500 causes backscatter electrons 130 to be generated. The backscatter electrons 130 are detected by one or more backscatter detectors 140. The detected backscatter electrons 130 are used to determine the structure and/or composition of the powder layer 500, including for example the packing and/or flatness of the powder layer 500. For example, the backscatter electrons 130 may be used to determine any defects in the powder layer 500.

In operation, the electron beam 110 may scan across the powder layer 500, thereby determining the topography of at least a part, for example all, of the powder layer 500, for example the surface of the powder layer 500. Such a process may be known as rastering the electron beam 110 across the powder layer 500. In this way, the electron beam 110 may be said to act like a scanning electron microscope.

The backscatter detector(s) 140 may measure, for example, the intensity of the interaction of the scanning electron beam 110 with the powder layer 500 and/or electromagnetic radiation released as a result of the scanning electron beam 110 impinging on the powder layer 500.

The backscatter detector(s) 140 may be in communication with a processor 600, as shown by way of example in the FIG. 2 arrangement. The processor 600 may be used to determine the structure and/or composition of the powder layer 500 from the back scatter electrons 130.

Figure 3:
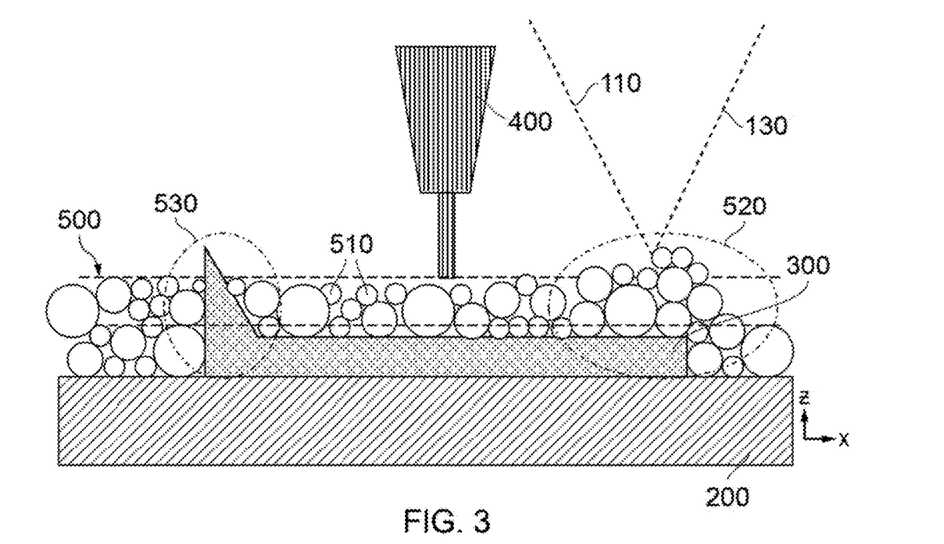
FIG. 3 shows a detailed side view of a powder layer.
Figure 4:
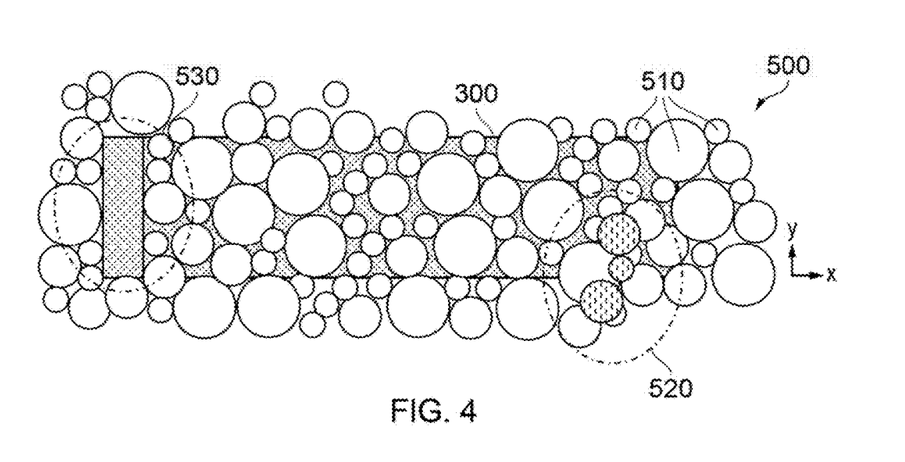
FIG. 4 shows a top view of the powder layer of FIG. 3.

FIG. 3 shows a more detailed side view of the powder layer 500. FIG. 4 shows a more detailed plan view of a powder layer 500. The powder layer 500 comprises powder particles 510. The powder particles 510 may be of varying sizes, as in the example of FIGS. 3 and 4. The powder particles 510 may be spherical, or generally spherical, also as shown in the example of FIGS. 3 and 4. The powder particles 510 may be any suitable material. The powder particles 510 may be conductive powder particles. For example, the powder particles 510 may be metallic powder particles 510. The term metallic powder particles may mean that the metal powder particles are solid metal particles, or metal coated particles, for example. Where the particles 510 are metallic particles, any suitable metal may be used. Purely by way of example, the particles 510 may comprise or consist of titanium and/or a titanium alloy and/or nickel and/or a nickel alloy. The thickness of the powder layer 500 may be dependent on the application, for example the type of component being manufactured and/or the type of ALM machine 100 being used. Purely by way of example, the powder layer 500 may have a thickness in the range of from 0.01 mm to 1 mm, for example 0.02 mm to 0.5 mm, for example 0.05 mm to 0.25 mm, for example 0.07 mm to 0.2 mm. However, it will be appreciated that powder layer thickness outside this range may be used.

In FIGS. 3 and 4, the powder layer 500 has been deposited onto a partially completed component 300, which comprises one or more previously melted and solidified layers 320. The component 300 itself sits on a base plate 200. A part of the powder layer 500 may be deposited onto powder from previous powder layers which has not been selectively melted, as in the FIG. 5 example. The general operation of the features shown in FIGS. 3 and 4 may be as described herein by way of example in relation to FIGS. 1 and 2.

FIGS. 3 and 4 show examples of defects that may occur in a powder layer 500. In particular, FIGS. 3 and 4 show a thick powder layer defect 520 and a swelling defect 530. It will be appreciated that other types of defects (such as, by way of example only, thin powder layer defects) may occur in the powder layer 500, and these other types of defects may also be identified using the present invention.

The thick powder layer defect 520 is caused by too many and/or too thick particles 510 being deposited at a given position in the powder layer 500. This could lead to defects in the finished component 300 after the selective melting and solidification, for example through incomplete melting at that position in the powder layer 500.

As shown in the FIG. 3 example, the scanning electron beam 110 may be used to detect the thick powder layer defect 520 through the backscatter electrons 130. When detected by the detectors 140, the backscatter electrons 130 may reveal the width (for example the diameter) of the individual particles 510 and/or the position of the individual particles in the direction perpendicular to the layer 500 (that is, the direction perpendicular to the baseplate 200 in the FIG. 3 example, or the "z" direction as indicated in FIG. 3). From this information, the position of each particle 510 in the z-direction and/or the local thickness of the layer 500 can be calculated. Such a calculation may be performed by a processor, such as the processor 600 described above in relation to FIG. 2.

The swelling defect 530 may be a defect in which the previously melted and solidified layer 320 protrudes or penetrate through the powder layer 500 being inspected. In this case, no powder particles, or at least very few powder particles 510 may be present at that position in the powder layer 500.

Figure 5:
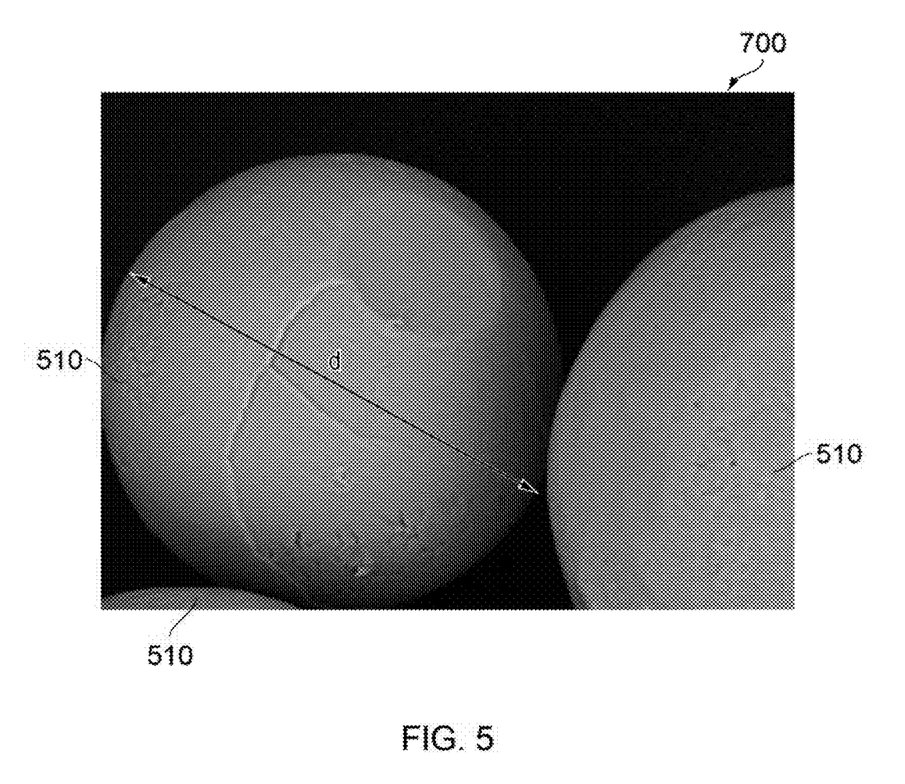
FIG. 5 shows an image of a powder particle produced using an electron beam in accordance with the invention.

FIG. 5 shows an image 700 of individual powder particles 510 produced using the information from the backscatter electrons 130. The image 700 may be generated using a processor 600, such as that shown in FIG. 2. FIG. 5 clearly shows that the size, for example the width, of the individual particles 510 can be calculated from the information provided by the detected backscatter electrons 130. In the FIG. 5 example, the particles are generally spherical, and the diameter d of a particle 510 is clearly indicated.

In some examples of the invention, the image 700 may not be generated, whereas in other examples the image 700 may be generated. Where no such image 700 is generated, the information from the detected backscatter electrons 130 may be used directly to calculate the information about the powder layer 500, such as the position of each particle 510 in the "z" direction and/or the local powder layer thickness.

If any defects 520, 530 in the powder layer 500 are detected, then a decision may be taken on whether or not to correct and/or remove the defects 520, 530 before performing the step of selective melting. The decision may be taken automatically, for example using a processor such as the processor 600 shown in FIG. 2 and/or may involve an operator of the ALM machine 10. As discussed elsewhere herein, the decision may be based on one or more parameters, for example parameters of the defects 520, 530 such as size and/or position. Also as discussed elsewhere herein, where the decision is taken to correct a defect, this may be performed in any suitable manner, for example by re-laying the powder layer 500 using the powder delivery device and/or raking mechanism, labelled 400 in FIG. 3.

Optionally, information relating to any detected defects 520, 530 (such as their position and/or size) may be stored, for example electronically. Such information may then be used (for example by a processor 600) to optimize parameters of the ALM process, such as, for example, the powder delivery process and/or the selective melting process. For example, if defects in the powder layer 500 are detected in the same position within two or more different powder layers, then these may be deemed to be recurring defects, which may be addressed by changing one or more parameters of the ALM process.

After the powder layer 500 has been inspected, with any defects detected removed as desired, the selective melting of the powder layer to form the next solid layer 320 may be performed, as described by way of example in relation to FIG. 1.

Optionally, after the selective melting has been performed, the resulting solidified layer 320 may be inspected to determine if any defects are present in the solidified layer 320. This may be performed before the base plate 200 is moved (or indexed) to the position for receiving the next powder layer 500, i.e. before the translatable support 210 is moved in the direction of arrow 220 in the FIG. 1 example.

Figure 6:
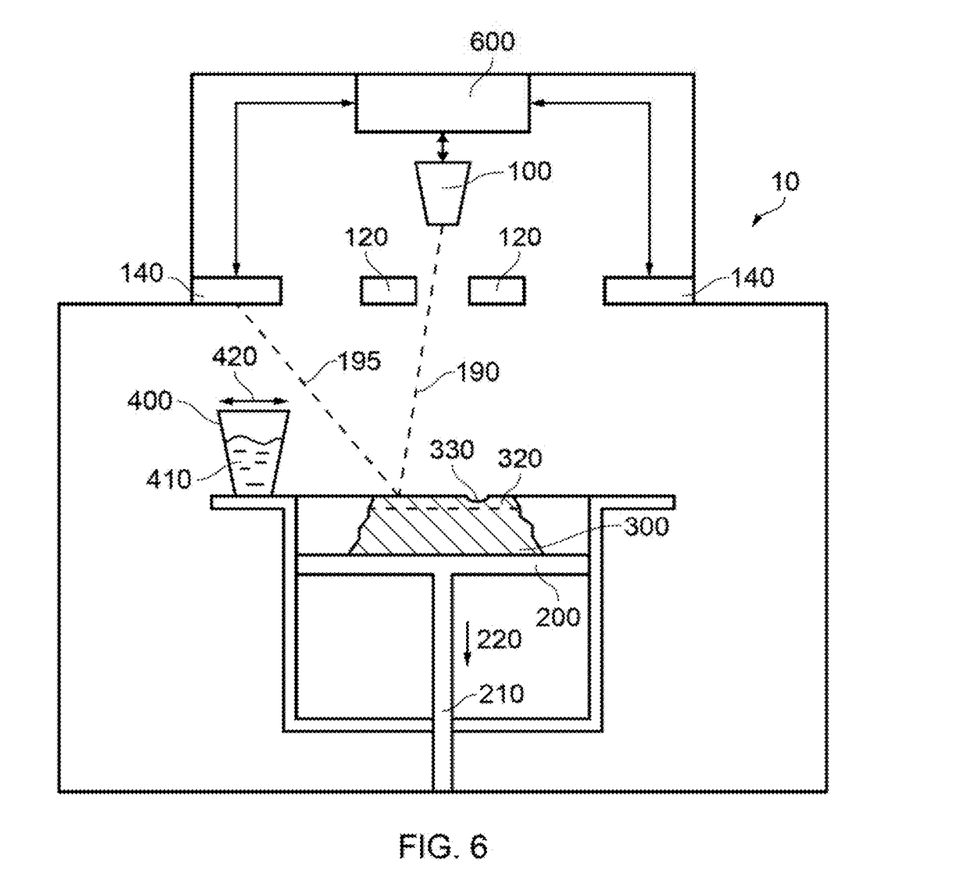
FIG. 6 shows an additive layer manufacture machine in accordance with the invention being used to detect defects in a solidified layer.

An inspection of the solid layer 320 may be performed using a solid layer scanning electron beam 190, as illustrated in FIG. 6. The solid layer scanning electron beam 190 may have a lower power and/or a lower intensity for example a lower maximum intensity) than the melting electron beam 180 used to perform the selective melting. As with the electron beam 110 for scanning the powder layer 500 prior to selective melting, the power and/or intensity of the solid layer scanning electron beam 190 may be insufficient to cause melting of the material on which it is incident.

In FIG. 6 the back-scattered electrons 195 from the interaction of the solid layer scanning electron beam 190 are detected by a detector 140. The pattern of the detected back-scattered electrons 196 can be used to determine the topography of the solidified layer 320. The detector 140 may measure, for example, the intensity of the interaction of the solid layer scanning electron beam 190 with the layer 320 and/or electromagnetic radiation released as a result of the solid layer scanning electron beam 190 impinging on the layer 320.

In operation, the solid layer scanning electron beam 190 may scan across the surface of the solidified layer 320, thereby determining the topography of at least a part, for example all, of the surface of the solidified layer 320. Such a process may be known as rastering the solid layer scanning electron beam 190 across the solidified layer 320. In this way, the solid layer scanning electron beam 190 may be said to act like a scanning electron microscope.

Thus, the back-scattered electrons 195 can be used to identify any defects that may be present in the solidified layer 320. At least some such defects may still be present despite any defects in the powder layer 500 having been identified and removed as required, as discussed above, for example due to errors or problems with the selective melting process. Such defects may include, for example, dimples and/or un-melted regions which may form porous zones in the finished component 300, and which may thus affect mechanical and/or geometrical properties of the finished component 300.

In a similar manner to that described above for the backscattered electrons 130 produced by the powder layer scanning electron beam 110, the detected back-scattered electrons 195 from the solid layer scanning electron beam 190 may be processed, for example using the processor 600, in order to identify defects. Imaging equipment may be used to show the topography of the surface of the layer 320 as determined by the detected back-scattered electrons 130.

Such imaging equipment may show defects as dark patches. The detected backscattered electrons 130 may be passed through an image processor, which may be a part of the processor 600. Such an image processor 600 may show dark patches where the detected back-scattered electrons 130 have a parameter above a threshold value, indicating a defect. It will be appreciated, however, that in some arrangements no image may be generated, and the information from the back-scattered electrons 130 may be acted upon directly.

Once any defects 330 in the solidified layer 320 have been identified, a decision may be taken as to how to address the defect 330. For example, at least a part of the layer 320 may be re-melted using the melting electron beam 180 in order to remove the defect(s) 330. For example, all of the layer 320 may be re-melted or just the region of the defect 330 (which may include a region surrounding the defect 330) may be re-melted. Before re-melting, additional metal powder 410 may or may not be added (for example in the region of the defect 330), for example using the hopper 400. The precise steps to be taken to remove a defect 330 (such as which region to re-melt, the scanning path of the melting electron beam 180 required to perform the re-melting, and whether to provide more powder 410 to the defect region) may be controlled by the processor 600.

By way of further example, the identified defect 330 may be simply left unchanged, and thus may not be removed. For example, once a defect 330 has been identified, a decision may be made with regard to whether to remove the defect (for example by re-melting), or to leave the defect unchanged. The decision may be based on, for example, the size of the defect 330, for example the cross-sectional area of the defect 330 and/or the depth of the defect 330. Additionally or alternatively, a decision regarding whether or not to remove a defect may be taken based on any other information, such as the shape of the defect 330 (for example whether its shape would be likely to lead to any crack initiation or propagation), and/or the location of the defect (for example whether it will be at or near to a surface of the finished component 300).

As with defects in the powder layer 500, the decision as to whether to remove a given defect 330 may be taken automatically (for example using an algorithm based on criteria such as those described herein), for example by the processor 600 based on the data provided from the detector 140. Additionally or alternatively, the decision may be taken by an operator.

Regardless of the decision, data representing the solidified layer 320 that is gathered by the electron detector 140 from the back-scatter electrons 195 may be stored, for example as electronic data. Data and/or images may be stored for the entire component, for example for each layer 320. Accordingly, the need to perform additional inspection and/or testing after the component 300 has been manufactured may be avoided, thereby saving time and expense. Furthermore, performing in-situ identification of defects using a solid layer scanning electron beam 190 may be more accurate than conventional non-destructive inspection (such as X-ray inspection) of the finished component 300. This may be particularly advantageous for components with thick walls or cross-sections, for which conventional non-destructive inspection may have limited capability. Where appropriate, images and/or data relating to the scanned layer(s) 320 may be stored both for the original layer 320, and for the layer 320 after defects 330 have been identified and removed.

Stored data representing the solidified layer 320 may be used to update and/or optimize the parameters of the selective melting step, for example for subsequent layers 320 and/or components 300. For example, the data may show that defects 330 occur at the same position in different layers 320. If such defects were not removed, they may stack up on top of each other, leading to significant porosity, and may thus be referred to as "stacking defects". This may indicate that one or more parameters used to melt the layer 320 using the melting electron beam 180 needs to be changed, or optimized, in order to avoid the defects 330 occurring at the corresponding positions in subsequent layers 320 and/or components 300. For example, a particular area of each layer 320 may not be receiving sufficient energy (for example energy per unit area or volume) from the melting electron beam 180 to correctly melt that area. In that case, one or more of many different parameters of the selective melting step may be adjusted to address the problem. Such parameters that may be adjusted include, for example, the power and/or intensity of the melting electron beam and/or the scanning (or rastering) speed of the melting electron beam, and/or the path (including the turning positions and/or rates) of the melting electron beam. In this way, recurring defects may be avoided. Any one or more of the processing and/or control steps involved in identifying such "stacking defects" and adjusting parameters accordingly may be carried out by a processor 600.

After any identified defects 330 have been removed, the layer 320 (or at least a part thereof, for example in the region of the identified defect(s) 330) may be re-scanned by the solid layer scanning electron beam 190 to check for any remaining defects 330. The process of identifying and optionally removing defects may then be iterated as required.

By identifying defects 330 in-situ in the solidified layers 320, not only may post-manufacture testing/inspection be avoided, but the final component 300 may be of a higher quality. For example, if the identified defects are subsequently removed (as described above, for example), then the final component 300 would contain fewer defects than would otherwise be the case, and thus may be considered to be of higher quality. For example, the finished component 300 may contain fewer voids. This may enable the components 300 to be used for applications requiring higher quality components (for example with better mechanical properties, such as strength and/or stiffness and/or durability). Additionally or alternatively, identifying and removing defects 330 in-situ may eliminate the need to perform additional manufacturing steps after the component 300 leaves the ALM machine 10. For example, identifying and removing defects 330 in-situ may avoid the need to perform an additional HIP step that may otherwise be required. These advantages also apply the identification and optional removal of defects 520, 530 from the powder layer 500, as described above, regardless of whether the subsequent step of identification and optional removal of defects 330 in the solid layer 320 is performed. Identification and optional removal of defects 520, 530 from the powder layer 500 may reduce the number of defects that are present in the solid layer 320 after selective melting.

Referring now back to FIGS. 1 and 2, the powder layer scanning electron beam 110 and the melting electron beam 180 may be generated using the same electron beam generator 100. Indeed, the solid layer scanning electron beam 190, where present, may also be generated using the same electron beam generator 100, as in the FIG. 6 example. As described elsewhere herein, the properties of the powder layer scanning electron beam 110 and the melting electron beam 180 and, where present, the solid layer scanning electron beam 190 may be different, for example in terms of energy and/or intensity (for example peak intensity). Thus, where the same electron beam generator 100 is used, the properties of the electron beams 110, 180, 190 may be controlled to be different, for example using the processor 600.

However, it will be appreciated that many alternative arrangements falling within the scope of the invention are possible. For example, the energy for melting the powder layer 500 may be provided by a source other than an electron beam, for example from a laser. In such arrangements, the powder layer electron beam source 100 would clearly be different to the source of the energy used to selectively melt the powder layer 500.

Figure 7:
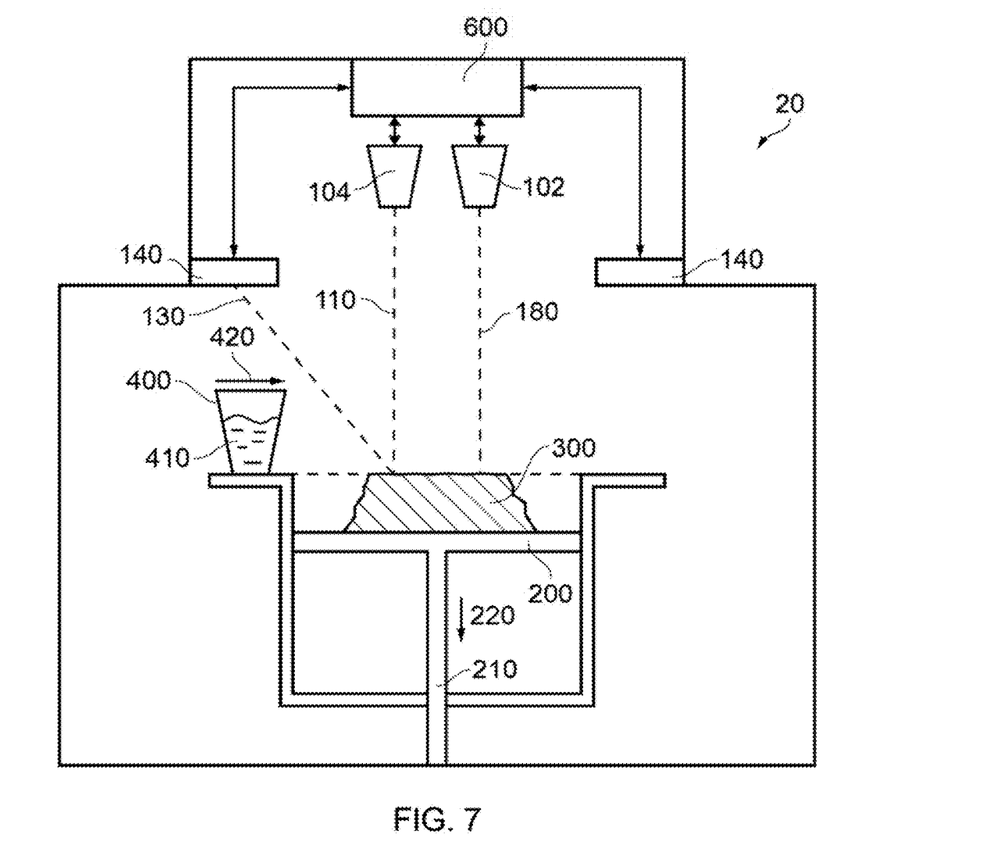
FIG. 7 shows an alternative additive layer manufacture machine in accordance with the invention.

Even in arrangements in which an electron beam 180 is used to selectively melt the powder layer 500, different sources 102, 104 may be used to generate the melting electron beam 180 and the powder layer scanning electron beam 110, as shown in the ALM machine of FIG. 7. The operation of the ALM machine 20 of FIG. 7, and the advantages associated therewith, is substantially the same as the ALM machine 10 discussed above, except in that the ALM machine 20 of FIG. 7 comprises two electron beam sources 102, 104, rather than just one electron beam source 100. As such, like features of the FIG. 7 and FIGS. 1, 2 and 6 ALM machines are given like reference numerals, and the discussion provided herein may relate to either example. Where a solid layer scanning electron beam 190 is also provided, this too may have a different electron beam source or, for example, may share the electron beam source 104 used to generate the powder layer scanning electron beam 110.

FIG. 7 shows both the melting and the powder layer scanning electron beams 180, 110, but it will be appreciated that the electron beams may operate at different times. For example, the powder layer scanning electron beam 110 may be used to scan a powder layer 500, and subsequently the melting electron beam 180 may be used to inspect that layer 320. However, the melting electron beam 180 may be generated by its electron beam source 102 at the same time that the powder layer scanning electron beam 110 is generated by its electron beam source 104. For example, the melting electron beam 180 may be used to selectively melt a part of a given powder layer 500 that has already been inspected by the powder layer scanning electron beam 110 at the same time as the powder layer scanning electron beam 110 is being used to inspect another part of the same powder layer 500.

The proposed method and apparatus described herein may be used to manufacture any desired component using ALM, for example any suitable component of a gas turbine engine. Purely by way of example, the proposed method and apparatus may be used to manufacture aerofoil components (including turbine or compressor rotating blades or static stators), or other rotating or static structures. Indeed, the proposed method and apparatus may be used for a great many different components, across a great many different industries. Purely by way of non-limitative example, the proposed method and apparatus may be used to manufacture brackets, mountings and/or fixtures, gearboxes and components thereof, structural components for vehicles (such as roll hoops and/or impact bars for cars), fluid filters (such as oil filters), fluid injection equipment (such as oil jet nozzles), seals, heat exchangers, head and facial implants, and joint replacements (such as acetabular hip joints/cups) and may be used in any industry, such as aerospace, automotive and medical.

It will be appreciated that many alternative and/or optional features other than those explicitly described herein may fall within the scope of the invention. For example, it will be apparent that the invention may involve the use of many alternative configurations of ALM machine (for example in terms of layout, electron beam generators and/or detectors and relative movement of parts). Furthermore, any feature described and/or claimed herein may be combined with any other compatible feature described in relation to the same or another embodiment.

I claim:

1. A method of manufacturing a component using additive layer manufacture, the method comprising:
   providing a powder layer to be melted in order to produce a layer of the component;
   scanning the powder layer using an electron beam;
   detecting back scattered electrons produced by the interaction of the electron beam with the powder layer;
   identifying, from the detected back scattered electrons, any defects in the powder layer to be melted;
   if a defect is identified in the powder layer, making a decision about whether or not to remove the identified defect in the powder layer, the decision being based on one or more predetermined criteria; then
   selectively melting at least a part of the powder layer so as to generate a solid layer of the component; and
   repeating the steps of: providing a powder layer; scanning the powder layer; detecting back scattered electrons; identifying defects in the powder layer; making a decision about whether or not to remove any identified defects; and selectively melting at least a part of the powder layer at least once so as to build up a shape corresponding to the component.

2. A method of manufacturing a component according to claim 1, wherein the power of the electron beam used to scan the powder layer is insufficient to cause melting of the powder layer.

3. A method of manufacturing a component according to claim 1, wherein the step of selectively melting at least a part of the powder layer is performed by an energy beam.

4. A method of manufacturing a component according to claim 3, wherein:
   the electron beam used to scan the powder layer is a first electron beam;
   the energy beam used to selectively melt at least a part of the powder layer is a second electron beam; and
   the power of the first electron beam is lower than the power of the second electron beam.

5. A method of manufacturing a component according to claim 4, wherein the first electron beam and the second electron beam are generated using the same electron beam source.

6. A method of manufacturing a component according to claim 1, further comprising:
   removing identified defects in the powder layer prior to selectively melting at least a part of the powder layer.

7. A method of manufacturing a component according to claim 1, wherein the decision is based at least in part on at least one of the size of the defect, the shape of the defect and the position of the defect.

8. A method of manufacturing a component according to claim 1, wherein the decision is taken by a machine.

9. A method of manufacturing a component according to claim 1, wherein the decision is taken by an operator of a machine.

10. A method of manufacturing a component according to claim 1, further comprising storing data relating to the scanned powder layer.

11. A method of manufacturing a component according to claim 10, further comprising:
    using the stored data to determine whether any defects have been identified at the same position in two or more different powder layers, such defects being recurring defects; and
    if any such recurring defects have been identified, adjusting one or more parameters of the step of providing a powder and/or adjusting one or more parameters of the selective melting step so as to avoid future recurring defects at that position.

12. A method of manufacturing a component according to claim 1, further comprising:
    identifying any defects in the solid layer by scanning the solid layer using a solid layer scanning electron beam and detecting back scattered electrons produced by the interaction of the solid layer scanning electron beam with the solid layer.

13. A method of manufacturing a component according to claim 12, wherein the power of the solid layer scanning electron beam is lower than the power of the second electron beam.

14. A method according to claim 1, wherein the powder layer is a metal powder layer.

15. A component manufactured using a method comprising the steps of claim 1.

16. A method of manufacturing a component using additive layer manufacture, the method comprising:
    providing a powder layer to be melted in order to produce a layer of the component;
    scanning the powder layer using an electron beam;
    detecting back scattered electrons produced by the interaction of the electron beam with the powder layer;
    identifying, from the detected back scattered electrons, any defects in the powder layer to be melted;
    storing data relating to the scanned powder layer;
    selectively melting at least a part of the powder layer so as to generate a solid layer of the component; and
    repeating the steps of: providing a powder layer; scanning the powder layer; detecting back scattered electrons; identifying defects in the powder layer; storing data relating to the scanned powder layer; and selectively melting at least a part of the powder layer at least once so as to build up a shape corresponding to the component;
    using the stored data to determine whether any defects have been identified at the same position in two or more different powder layers, such defects being recurring defects; and
    if any such recurring defects have been identified, adjusting one or more parameters of the step of providing a powder and/or adjusting one or more parameters of the selective melting step so as to avoid future recurring defects at that position.

17. A method of manufacturing a component according to claim 16, wherein the power of the electron beam used to scan the powder layer is insufficient to cause melting of the powder layer.

18. A method of manufacturing a component according to claim 16, wherein the step of selectively melting at least a part of the powder layer is performed by an energy beam.

19. A method of manufacturing a component according to claim 18, wherein:
- the electron beam used to scan the powder layer is a first electron beam;
- the energy beam used to selectively melt at least a part of the powder layer is a second electron beam; and
- the power of the first electron beam is lower than the power of the second electron beam.

20. A method of manufacturing a component according to claim 16, further comprising:
- removing identified defects in the powder layer prior to selectively melting at least a part of the powder layer.

* * * * *